United States Patent [19]

Stein

[11] Patent Number: 5,475,044
[45] Date of Patent: Dec. 12, 1995

[54] ADDITION-CURABLE SILICON ADHESIVE COMPOSITIONS AND BIS(TRIALKOXYSILYL)ALPHA-AMINO ESTER ADHESION PROMOTERS

[75] Inventor: Judith Stein, Schenectady, N.Y.

[73] Assignee: General Electric Company, Schenectady, N.Y.

[21] Appl. No.: 368,405

[22] Filed: Dec. 29, 1994

Related U.S. Application Data

[63] Continuation of Ser. No. 169,271, Dec. 20, 1993, abandoned.

[51] Int. Cl.$^6$ ..................................................... C08K 5/54
[52] U.S. Cl. .......................... 524/188; 524/262; 524/268; 524/588; 525/478; 528/15; 528/31; 528/32
[58] Field of Search ................................. 524/188, 262, 524/268, 588; 525/478; 528/15, 31, 32

[56] References Cited

U.S. PATENT DOCUMENTS 5,164,461  11/1992  Mitchell et al. .......................... 528/15
5,173,529  12/1992  Fujiki et al. ............................. 524/188

Primary Examiner—Melvyn J. Marquis
Assistant Examiner—Mark D. Sweet
Attorney, Agent, or Firm—William H. Pittman

[57] ABSTRACT

Addition-curable platinum group metal catalyzed silicone compositions are provided which utilize a bis(trialkyloxysilyl)alpha-amino ester as an adhesion promoter. Cohesive bonding is effected on both plastic and metal substrates at temperatures of about 100° C. in an hour or less.

5 Claims, No Drawings

ADDITION-CURABLE SILICON ADHESIVE COMPOSITIONS AND BIS(TRIALKOXYSILYL)ALPHA-AMINO ESTER ADHESION PROMOTERS

This application is a continuation of application Ser. No. 08/169,271 filed Dec. 20, 1993, now abandoned.

BACKGROUND OF THE INVENTION

The present invention relates to platinum group metal catalyzed addition-curable silicone adhesive compositions employing a bis (trialkoxysilyl)alpha-amino ester as an adhesion promoter.

As shown by Kasuya, U.S. Pat. No. 3,284,406, the adhesion of a cured platinum catalyzed addition-curable silicone composition onto a substrate can be achieved by effecting the cure of the silicone composition at a temperature such as 120° C. for at least one hour Schulz, U.S. Pat. No. 4,087,585 is directed to self-adhering addition-curable silicone compositions which cure at 100° C. after several hours and at temperatures up to 150° C. for shorter cure periods. Satisfactory adhesion is shown on metallic substrates, such as aluminum, as a result of using an epoxy-containing alkoxysilane as an adhesion promoter.

It would be desirable to provide addition-curable silicone adhesive compositions which could be applied onto a variety of unprimed substrates, such as plastic or metal, to effect a satisfactory cure in about an hour and at a temperature of about 100° C. or less. In addition, it also would be desirable to produce a silicone substrate composite having a silicone layer which would fail cohesively instead of adhesively when tested. As used hereinafter, the expression "adhesive failure" means the silicone layer can be cleanly separated from the substrate, while in a "cohesive failure" rupture can occur in the silicone layer or in the substrate when separation is achieved.

SUMMARY OF THE INVENTION

The present invention is based on the discovery that certain bis(trialkoxysilyl)alpha-amino esters have been found to be effective as adhesion promoters when used in a platinum catalyzed addition-curable silicone composition, as defined hereinafter. In addition, the resulting curable composition has been found to provide a silicone adhesive which can be cured at temperatures of about 100° C. or less in about 1 hour to produce a cohesive bond when cured in contact with a plastic or metallic substrate.

STATEMENT OF THE INVENTION

There is provided by the present invention, a platinum group metal catalyzed addition-curable silicone composition, comprising by weight, (A) 100 parts of a vinyl-containing polydiorganosiloxane composition comprising,
 (1) about 50 to about 100 parts of an essentially cyclic-free vinyl-terminated polydiorganosiloxane having the general formula, $$(R)_2V_iSiO[(R)_2SiO]_m[RV_iSiO]_nSi(R)_2V_i, \tag{1}$$

where $V_i$ is a vinyl radical, R is selected from the class consisting of alkyl radicals having 1 to 8 carbon atoms, phenyl radicals, fluoroalkyl radicals having 3 to 10 carbon atoms and mixtures thereof, "m+n" has a value sufficient to provide a polydiorganosiloxane having viscosity of 100 to about 100,000 centipoise at 25° C., and a vinyl content of from about 0.02 to about 2.0 weight %, and (2) from about 0 to about 50 parts of a solid, benzene-soluble vinyl-containing resin copolymer comprising,

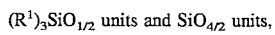

where $R^1$ is a vinyl radical, or a monovalent hydrocarbon radical free of aliphatic unsaturation and containing no more than six carbon atoms, the ratio of $(R^1)_3SiO_{1/2}$ units to $SiO_{4/2}$ units being from about 0.5:1 to about 1.5:1, and the vinyl-containing resin having a vinyl content of from about 1.5 to about 3.5% by weight, (B) from about 1 to about 20 parts of a hydrogen-containing polysiloxane having an average unit formula, $$R^2{}_aH_bSiO_{(4-a-b)/2}, \tag{2}$$

where $R^2$ is a monovalent hydrocarbon radical, or halogenated monovalent hydrocarbon radical having from 1 to about 10 carbon atoms and free of aliphatic unsaturation, "a" has a value of from about 0 to about 3, "b" has a value of from about 0 to about 3, and the sum of "a"+"b" has a value of from 0 to 3, (C) a catalytic amount of a platinum group metal hydrosilylation catalyst, (D) an effective amount of a bis [trialkyloxysilyl]alpha-amino ester adhesion promoter having the formula, $$R^3O)_3SiR^4OC(O)CH_2N(H)R^5Si(OR^3)_3, \tag{3}$$

where $R^3$ is selected from the same or different $C_{(1-4)}$ alkyl radicals and $R^4$ and $R^5$ are selected from the same or different $C_{(2-8)}$ alkylene radicals, (E) from about 0 to about 200 parts of an extending filler, and (F) from about 0 to about 50 parts of a reinforcing filler, and in the absence of (A)(2), an amount effective for reinforcement.

In a further aspect of the invention, there are provided bis(trialkyloxysilyl)alpha-amino esters and a method for making. These compounds can be made by initially effecting reaction under ambient conditions, and under an inert atmosphere, between an alpha-halo acyl halide, such as alpha-bromo acetyl bromide and an alkenyl alcohol, such as allyl alcohol, to form the corresponding alpha-halo alkenyl ester. Reaction can then be effected between the ester and an alkenyl amine, such as allylamine at temperatures of about 0° C. in an inert atmosphere in the presence of a base, such as triethylamine, to form the corresponding bis(alkenyl)alpha-amino ester. Addition of a trialkoxysilane, such as trimethoxysilane, can be effected by use of a hydrosilylation platinum catalyst.

The addition-curable compositions of the present invention can be used as adhesives in industrial multilayered laminates. These adhesives also can adhere to substrates that are in contact with the compositions during curing. Substrates which are included are glass, metals, metal oxides, and plastics. Among the plastics, there are included, polyetherimides, phenolic resins, epoxy resins, polyamides, unsaturated polyesters, poly(ethylene terephthalate), polyphenylene sulfide, polyacetals, and polyimides.

There are included within the bis (trialkoxysilyl) alpha-amino esters of formula (3), referred to hereinafter as the "adhesion promoters", compounds such as,

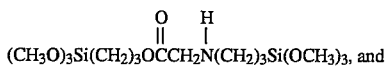

and

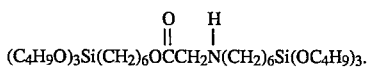

An effective amount of the adhesion promoter is 0.6 to 2 parts by weight of adhesion promoter, per 100 parts by weight of the platinum group metal catalyzed addition-curable adhesion composition, referred to hereinafter as the "addition-curable composition".

The vinyl-terminated polydiorganosiloxane of formula (1) preferably has a viscosity of from about 3,000 to about 95,000 centipoise at 25° C. Radicals represented by R are preferably alkyl radicals of 1 to about 4 carbon atoms, and most preferably methyl.

Component (A) (2) is a vinyl-containing benzene-soluble siloxane resin containing $(R^1)_3SiO_{1/2}$ units, or (M units), and $SiO_{4/2}$ units, or (Q units), where each $R^1$ is a vinyl radical, or a monovalent hydrocarbon radical free of aliphatic unsaturation and containing no more than six carbon atoms, the ratio of $R^1)_3SiO_{1/2}$ units to $SiO_{4/2}$ units being from about 0.5: 1 to about 1.5: 1; the resin having a vinyl content of from about 1.5 to about 3.5% by weight. Component (A) (2) also is referred to as the "vinyl-containing MQ resin".

Component (A) (2) may further contain (i) $R^1SiO_{3/2}$ units, (ii) $(R^1)_2SiO_1$ units, or both (i) and (ii), the $R^1)_2SiO_1$ units being present in an amount equal to from about 0 to about 10 mole percent based on the total number of moles of siloxane units in (A) (2), and the $R^1SiO_{3/2}$ units being present in an amount equal to from about 0 to about 10 mole percent based on the total number of moles of siloxane units in (A)(2).

Component (A) comprises from about 50 to about 100, and preferably from about 56 to about 100, and most preferably from about 60 to about 75, parts by weight of (A) (1) and from about 0 to about 50, preferably from about 0 to about 40, and most preferably from about 25 to about 40, parts by weight of (A)(2).

In one preferred embodiment of the composition of the present invention, component (A) comprises from about 60 to about 75 parts by weight of (1) a vinyl terminated polydiorganosiloxane having a viscosity of 65,000 to about 95,000 centipoise at 25° C., and (2) from about 25 to about 40 parts by weight of the vinyl-containing MQ resin.

In another preferred embodiment of the composition of the present invention, component (A) comprises from about 60 to about 75 parts by weight of (1) a vinyl terminated polydiorganosiloxane having a viscosity of 3000 to about 5000 centipoise at 25° C., and (2) from about 25 to about 40 parts by weight of the vinyl-containing MQ resin.

In a further preferred embodiment of the composition of the present invention, component (A) comprises 100 parts by weight of:

(1) a blend containing from about 25 to about 35 parts by weight of the vinyl-containing polydiorganosiloxane of formula (1) having a viscosity of 3000 to about 5000 centipoise of 25° C. and from about 65 to about 75 parts by weight of a vinyl-containing polydiorganosiloxane of formula (1) above and having a viscosity of 75,000 to about 95,000 centipoise at 25° C., the total amount of (1) being 100 parts by weight. Preferably, component (A) will additionally contain, (2) from about 5.5 to about 7.5 parts by weight of a low viscosity polydiorganosiloxane composition having an average of at least one vinyldiorganosiloxy end group, a vinyl content of from about 0.2 to about 0.3% by weight and a viscosity of from about 400 to about 700 centipoise at 25° C., (3) from about 5.5 to about 7.5 parts by weight of a low viscosity vinyldiorgano end-stopped, diorganopolysiloxane having a vinyl content of from about 1.4 to about 2.0% by weight and a viscosity of from about 300 to about 600 centipoise at 25° C. and free of the vinyl containing MQ resin. Preferably, reinforcing filler is present in the composition containing (A)–(E), if (A) contains this vinyl polymer blend.

The hydrogen-containing polysiloxane of formula (2) functions as a crosslinking agent. A preferred hydrogen containing polysiloxane has the formula,

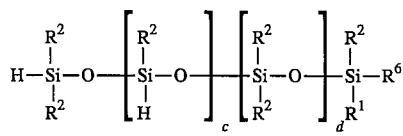

(4)

where $R^2$ is as defined above, $R^6$ is $R^2$ or hydrogen, "c" and "d" have values which are sufficient when added together to provide a viscosity of from about 10 to about 1000, and as a hydrogen containing polysiloxane fluid, has a hydrogen content of from about 0.02 to about 1.6% by weight.

The hydrogen-containing polysiloxane fluid of formula (4), can be used as a hydride cross-linking agent in the present invention. In formulas (2) and (4) above, $R^2$ is preferably selected from alkyl radicals of 1 to 8 carbon atoms, phenyl, fluoroalkyl radicals of 3 to 10 carbon atoms and hydrogen, the preferred fluoroalkyl radical being trifluoropropyl. Most preferably, $R^2$ represents a methyl radical.

The hydrogen-containing polysiloxane fluid of formula (4) can have a viscosity of from about 10 to about 1000 and preferably from about 10 to about 150 centipoise at 25° C.

Other hydrogen-containing polysiloxane fluids which can be used in the present invention include fluid siloxane copolymer resins comprised of $R^1)_3SiO_{1/2}$("M") units, $SiO_{4/2}$ ("Q") units, and units such as $H(R^2)_2SiO_{1/2}$ ("$M^H$"), $HR^2SiO_1$ ("$D^H$") and $R^2)_2SiO_1$ ("D") and mixtures of fluid polyorganosiloxanes and fluid siloxane copolymer resins described in U.S. Pat. No. 3,627,851, which is hereby incorporated by reference herein. The preferred resins are known as $M^HQ$ resins, which comprise diorganohydrogensiloxy units ($M^H$) units and $SiO_{4/2}$ (Q) units, wherein the ratio of diorganohydrogensiloxy units ($M^H$) units to Q units is from 0.4:1.0 to 2.0:1.00 inclusive. Hydrogen containing polysiloxanes having at least one $R^1$ group, preferably, a methyl group, bonded to silicon which bears at least one reactive hydrogen atom are preferred. It is to be understood that the hydrogen containing polysiloxane can be a single compound or a mixture of compounds. Additional hydrogen containing polysiloxanes suitable for use in the present invention are disclosed, for example, in U.S. Pat No. 4,061,609 to Bobear, which is hereby incorporated by reference herein.

Further examples of hydrogen-containing polysiloxanes which can be used in the present invention are linear triorgano endstopped organohydrogen-polysiloxane fluids having a viscosity of from about 15 to about 40 centistokes at 25° C., and a hydrogen content of 1.6% by weight. These hydrogen containing polysiloxanes generally have the formula,

where $R^2$ is as previously defined herein and "e" is a number sufficient to provide a viscosity of from about 15 to about 40 centistokes at 25° C.

It is preferred that the hydrogen-containing polysiloxane of formulas (4) and (5) have a hydride content of 0.05 to 1.6%, and more preferably of 0.1 to 1% by weight. In instances where the vinyl containing polydiorganopolysiloxane of formula (1) has a viscosity of between 3000 to 5000 centipoise and the hydrogen containing polysiloxane is a triorgano end-stopped organohydrogensiloxane, the SiH:SiVinyl ratio is preferably at least 2.1:1, while about 2.1:1 to about 10.1, or from about 2.1:1 to about 3.5: 1 is particularly preferred.

Component (C) of the adhesion composition of the present invention which promotes the hydrosilylation reaction is a platinum group metal catalyst. Additional catalysts for facilitating the hydrosilylation curing reaction include precious metal catalysts such as those which use ruthenium, rhodium, palladium, osmium, and iridium, and complexes of these metals. Examples of suitable hydrosilylation catalysts for use in the present invention are disclosed, for example in U.S. Pat. Nos. 3,159,601 and 3,159,662 (Ashby); 3,220,970 (Lamoreaux); 3,775,452 (Karstedt) , 3,516,946 (Modic) , and 4,029,629 (Jeram); all of the foregoing patents being hereby incorporated by reference herein.

Preferably, the hydrosilylation catalyst is a platinum containing catalyst. A preferred platinum-containing catalyst is a platinum-octanol complex containing 90.9 weight % octyl alcohol and 9.1 weight % chloroplatinic acid.

Another preferred platinum-containing catalyst is a platinum complex formed by reacting chloroplatinic acid containing 4 moles of water of hydration with tetravinylcyclotetrasiloxane in the presence of sodium bicarbonate in an ethanol solution. This catalyst is disclosed in U.S. Pat. No. 3,775,452 to Karstedt, which is hereby incorporated by reference herein.

The catalyst must be used in a catalytic amount, which is that amount sufficient to promote the hydrosilylation reaction. Generally, there must be utilized at least 0.1 part per million of a platinum catalyst, and preferably from 5 ppm to 250 ppm, in terms of parts of platinum metal based on the weight of hydrosilylation mixture. Inhibitors,such as acetylenic alcohols, amines, and cyanurates also can be employed when used in an effective amount.

The composition of the present invention may also contain any of the conventional (E) extending and/or (F) reinforcing fillers. The composition contains from about 0 to about 200 and preferably from about 10 to about 100 parts by weight of (E) an extending filler, and from about 0 to about 50, and preferably from about 20 to about 50 parts by weight of (F) a reinforcing filler.

Examples of extending fillers (E) useful herein include alpha quartz, crushed quartz, aluminum oxide, aluminum silicate, zirconium silicate, magnesium oxide, zinc oxide, talc, diatomaceous earth, iron oxide, calcium carbonate, clay, titania, zirconia, mica, glass, such as ground glass or glass fiber, sand, carbon black, graphite barium sulfate, zinc sulfate, wood flour, cork, fluorocarbon polymer powder and the like. The preferred extending filler for use in the present invention is alpha quartz.

Examples of reinforcing fillers (F) include silica, such as fumed silica and precipitated silica, and treated silica fillers such as fumed or precipitated silica that has been reacted with, e.g., an organohalosilane, a disiloxane, or a disilazane. Fumed silica is particularly effective as a reinforcing filler for the silicone component of the present invention. Particularly preferred, is a fumed silica which has been initially treated with a cyclic polysiloxane, e.g., dimethylcyclic tetramer, according to the methods known in the art, for example, as taught in U.S. Pat. No. 2,938,009 (Lucas), which is incorporated by reference herein, and then treated with a silazane, e.g., hexamethyldisilazane, for example, as taught in U.S. Pat. Nos. 3,635,743 (Smith) and 3,847,848 (Beers), which are both incorporated by reference. This treatment has been found to remove most of the free silanols on the surface of the tetramer treated silica.

The composition of the present invention can be prepared by homogeneously mixing components (A)–(F) and any optional ingredients, using suitable mixing means, such as a spatula, a drum roller, a mechanical stirrer, a three-roll mill, a sigma blade mixer, a bread dough mixer and a two-roll mill.

The order of mixing components (A)–(F) is not critical, however, it is preferred that components (B) and (C) be brought together in the presence of component (D), most preferable in a final mixing step. Thus, it is possible to mix all components in one mixing step immediately prior to the intended use of the curable composition. Alternatively, certain components can be premixed to form two or more packages which can be stored, if desired, and then mixed in a final step immediately prior to the intended use thereof.

It is preferred to mix components (C), (D), and a portion of component (A), along with certain optional components, such as fillers and solvents, to provide a first package. Separately, component (B), along with the remaining portion of component (A), if any, can be mixed to provide a second package. These two packages can then be stored until the composition of this invention is desired and then homogeneously mixed.

The addition-curable silicone compositions of the invention will directly self-bond in the absence of primer to various plastic, metal, glass, and masonry substrates. Examples of metal substrates include metal substrates selected from copper, alclad aluminum, anodized aluminum, galvanized steel, cold-rolled steel, cast aluminum, and cast magnesium. In particular instances it is preferred to "condition" certain substrates such as polyetherimide by treating the polyetherimide substrate with a 5M KOH solution at 70° C. for 5 minutes followed by a rinse. The thickness of the adhesive composition on a substrate is typically from about 20 to about 60 mils.

The addition-curable compositions of the present invention can be applied onto the surface of the substrate by any suitable means such as rolling, spreading, spraying, and the like, and cured as described above. After application of the adhesive composition onto the substrate, the composition can be cured at a temperature in the range of about 50° C. to 100° C. over a period of about 10 to 30 minutes.

In order that those skilled in the art may better understand the practice of the present invention, the following examples are given by way of illustration and not by way of limitation. All parts are by weight.

EXAMPLE 1

There was added dropwise, 15 g of allyl alcohol to 20 g of alpha-bromo acetyl bromide under a nitrogen atmosphere at ambient temperatures. The mixture was stirred for three hours followed by the removal of excess allyl alcohol in vacuo. There was obtained 15 g of product. Based on $^1$H NMR spectra, the product was the corresponding allyl ester of alpha-bromo acetic acid.

There was added dropwise, under an inert atmosphere, a mixture of 1.71 g of allylamine and 3.03 g of triethylamine to 5.4 g of the above alpha-bromo ester in 50 mls of diethylether while the solution was stirred. A white precipitate formed. After 14 hours, the mixture was filtered and the solvent removed in vacuo. The mono ester was separated from the diester by distillation in vacuo at 40° C.

There was added 2.7 uL of a solution of a platinum catalyst (5.92% Pt) shown in Karstedt U. S. Pat. No 3,775, 452 and 1 ml of trimethoxysilane to 0.5 g of the above diallyl ester of alpha-amino acetic acid. The mixture was heated at 70° C. for 12 hours. There was obtained 1.0 g of product Based on $^1$H NMR the product was a bis (trimethoxysilyl)alpha-amino ester having the formula, $(CH_3O)_3SiCH_2CH_2CH_2N(H)CH_2C(O)OCH_2CH_2CH_2Si(OCH_3)_3$.

EXAMPLE 2

A thermally activated addition curable silicone formulation was prepared by adding 0.23 g of a methylhydrogensiloxydimethylsiloxy copolmer having a hydrogen content of about 0.8% by weight to a mixture of 13 g of a mixture of a polydimethylsiloxane having terminal dimethylvinylsiloxy units and a viscosity about 40,000 centipoise and 20% by weight of the mixture of fumed silica treated with octamethylcyclotetrasiloxane, 10 ppm of platinum as shown in example 1, 1 uL of 3,5-dimethyl-1-hexyn-3-ol and 0.12 g of the alpha-amino ester adhesion promoter of example 1. The mixture was degassed by two cycles of evacuation/centrufigation.

Lap shears of 1"×0.5" coupons of various substrates were tested after they had been wiped with isopropanol, and treated with the above addition-curable formulation-Cure was effected at 100° C./1hour The resulting composites were tested on an Instron 4202 using a crosshead speed of 0.5"/min. The following results were obtained, where polyester is Valox® polyester and polycarbonate is Lexan® polycarbonate, both thermoplastics being made by GE Plastics Div.

| Substrate | Failure Mode | Lap Shear Strength (psi) |
|---|---|---|
| Alclad | Cohesive | 320, 454 |
| Steel | Cohesive | 298 |
| Polyester | Cohesive | 390 |
| Polycarbonate | Adhesive | — |

Adhesive failure was obtained in all instances where the adhesion promoter was excluded from the addition-curable composition. However, a degree of adhesion was obtained on a polycarbonate substrate even though the failure was adhesive.

Although the above examples are directed to only a few of the very many variables which can be used in the practice of the present invention, it should be understood that the present invention is directed to a much broader variety of bis(trialkoxysilyl)alpha-amino ester adhesion promoters and addition-curable organopolysiloxane compositions containing such adhesion promoters as shown in the description preceding these examples.

What is claimed is:
1. An addition-curable composition consisting essentially of, by weight:
   (A) 100 parts of a vinyl-containing polydiorganosiloxane composition comprising:
      (1) about 50–100 parts of an essentially cyclic-free vinyl-terminated polydiorganosiloxane having the general formula,

$R_2ViSiO(R_2SiO)_m(RViSiO)_nSiR_2Vi$, where Vi is a vinyl radical; R is selected from the class consisting of alkyl radicals having 1 to 8 carbon atoms, phenyl radicals, fluoroalkyl radicals having 3 to 10 carbon atoms and mixtures thereof and the value of m+n is sufficient to provide a viscosity of 100–100,000 centipoise at 25° C. and a vinyl content of about 0.02–2.0& by weight; and
      (2) about 0–50 parts of a solid, benzene-soluble vinyl-containing resin copolymer comprising $(R^1)_3SiO_{1/2}$ units and $SiO_{4/2}$ units, where $R^1$ is a vinyl radical or a monovalent hydrocarbon radical free of aliphatic unsaturation and containing no more than six carbon atoms, the ratio of $(R^1)_3$ $SiO_{1/2}$ units to $SiO_{4/2}$ units being about 0.5–1.5:1; said copolymer having a vinyl content of about 1.5–3.5% by weight;
   (B) about 1–20 parts of a hydrogen-containing polysiloxane having an average unit formula, $(R^2)_aH_bSiO_{(4-a-b)/2}$, where $R^2$ is a monovalent hydrocarbon radical or halogenated monovalent hydrocarbon radical having about 1–10 carbon atoms and free of aliphatic unsaturation, a has a value of about 0–3, b has a value of about 0–3 and a+b has a value of 0–3;
   (C) a catalytic amount of a hydrosilylation catalyst,
   (D) 0.6–2.0 parts, per 100 parts of said addition-curable composition, of a bis(trialkyloxysilyl)alpha-amino ester having the formula $(R^3O)_3SiR^4OC(O)CH_2N(H)R^5Si(OR^3)_3$, where $R^3$ is selected from the same or different $C_{1-4}$ alkyl radicals and $R^4$ and $R^5$ are selected from the same or different $C_{2-8}$ alkylene radicals;
   (E) about 0–200 parts of an extending filler and
   (F) about 0–50 parts of a reinforcing filler, and in the absence of (A)(2), an amount thereof effective for reinforcement.

2. An addition-curable composition in accordance with claim 1, where the vinyl-containing polydiorganopolysiloxane is a vinyl-containing polydimethylsiloxane.

3. An addition-curable composition in accordance with claim 1, where the solid, benzene-soluble vinyl-containing resin comprises a mixture of $(CH_3)_3SiO_{1/2}$ units and $Vi(CH_3)_2SiO_{1/2}$ units and $SiO_2$ units.

4. An addition-curable composition in accordance with claim 1, where the hydrosilylation catalyst is a platinum catalyst.

5. An addition-curable composition in accordance with claim 1, where $(CH_3O)_3SiCH_2CH_2CH_2N(H)CH_2C(O)OCH_2CH_2CH_2Si(OCH_3)_3$ is the adhesion promoter.

* * * * *

UNITED STATES PATENT AND TRADEMARK OFFICE
CERTIFICATE OF CORRECTION

PATENT NO. : 5,475,044

DATED : December 12, 1995

INVENTOR(S) : Stein

It is certified that error appears in the above-indentified patent and that said Letters Patent is hereby corrected as shown below:

Title page and column 1, line 1, "SILICON" should read --SILICONE--.

Signed and Sealed this

Sixteenth Day of April, 1996

Attest:

BRUCE LEHMAN

Attesting Officer

Commissioner of Patents and Trademarks